United States Patent

Villar et al.

[11] Patent Number: 6,063,104
[45] Date of Patent: *May 16, 2000

[54] DETACHABLE, VARYING FLEXIBILITY, ANEURYSM NECK BRIDGE

[75] Inventors: Francisco S. Villar, Newark; Nestor Aganon; Nga T. Doan, both of San Jose; Robert M. Abrams, Sunnyvale; Clifford Teoh, Daly City, all of Calif.

[73] Assignee: Target Therapeutics, Inc., Fremont, Calif.

[*] Notice: This patent is subject to a terminal disclaimer.

[21] Appl. No.: 09/313,958

[22] Filed: May 18, 1999

Related U.S. Application Data

[63] Continuation of application No. 09/103,472, Jun. 24, 1998, Pat. No. 5,935,148.

[51] Int. Cl.⁷ .................................................. A61B 17/03
[52] U.S. Cl. ............................................. 606/213; 623/11
[58] Field of Search ................................. 606/198, 213, 606/215; 623/11

[56] References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,753,700 | 8/1973 | Harrison et al. . |
| 4,739,768 | 4/1988 | Engelson . |
| 4,744,364 | 5/1988 | Kensey ..................................... 606/213 |
| 4,994,069 | 2/1991 | Ritchart et al. ............................ 623/11 |
| 5,122,136 | 6/1992 | Guglielmi et al. . |
| 5,226,911 | 7/1993 | Chee et al. ................................ 606/198 |
| 5,250,071 | 10/1993 | Palermo . |
| 5,261,916 | 11/1993 | Engelson . |
| 5,354,295 | 10/1994 | Guglielmi et al. . |
| 5,370,660 | 12/1994 | Weinstein ................................ 606/215 |
| 5,451,235 | 9/1995 | Lock et al. .............................. 606/213 |
| 5,624,449 | 4/1997 | Pham et al. . |
| 5,643,254 | 7/1997 | Scheldrup et al. . |
| 5,669,254 | 9/1997 | Scheldrup et al. . |
| 5,690,666 | 11/1997 | Berenstein et al. . |
| 5,709,707 | 1/1998 | Lock et al. .............................. 606/213 |
| 5,716,408 | 2/1998 | Eldridge et al. ......................... 606/213 |
| 5,741,297 | 4/1998 | Simon .................................... 606/213 |
| 5,749,874 | 5/1998 | Schwartz ................................ 606/215 |
| 5,749,894 | 5/1998 | Engelson ................................ 606/213 |
| 5,792,154 | 8/1998 | Doan et al. ............................. 606/213 |
| 5,935,148 | 8/1999 | Villar et al. ............................. 606/213 |

*Primary Examiner*—Paul J. Hirsch
*Attorney, Agent, or Firm*—Morrison & Foerster LLP

[57] ABSTRACT

This is a device for bridging the neck of either a wide-necked or narrow-necked aneurysm as may be found in the vasculature. It may be used to stabilize the placement of vaso-occlusive devices such as helically wound coils in the aneurysm or may be used to, at least partially, close the aneurysm neck. The vaso-occlusive devices, commonly helically wound coils, are delivered by a core wire which is linked to the coils by an electrolytically severable joint. The core wire will often be insulated. The retainer assembly itself is also attached to another delivery device, such as a core wire, and desirably is severed from the core or delivery wire by the use of another electrolytically severable joint. The inventive neck bridge typically has a number of array elements which are intended to be resident within the aneurysm after the device is deployed from the distal end of a catheter. Central to this invention is the use of array elements having differing flexibility or constituent members of the array elements, e.g., wires making up the array elements, which are of differing flexibilities. After deployment of this retainer, the aneurysm may be at least partially filled with vaso-occlusive devices such as helically wound coils.

16 Claims, 4 Drawing Sheets

DETACHABLE, VARYING FLEXIBILITY, ANEURYSM NECK BRIDGE

This application is a continuation of U.S. patent application Ser. No. 09/103,472, entitled "DETACHABLE, VARYING FLEXIBILITY, ANEURYSM NECK BRIDGE", filed Jun. 24, 1998, now U.S. Pat. No. 5,935,148.

FIELD OF THE INVENTION

This invention is a device for bridging the neck of either a wide-necked or narrow-necked aneurysm as may be found in the vasculature. It may be used to stabilize the placement of vaso-occlusive devices such as helically wound coils in the aneurysm or may be used to, at least partially, close the aneurysm neck. The vaso-occlusive devices, commonly helically wound coils, are delivered by a core wire which is linked to the coils by an electrolytically severable joint. The core wire will often be insulated. The retainer assembly itself is also attached to another delivery device, such as a core wire, and desirably is severed from the core or delivery wire by the use of another electrolytically severable joint. The inventive neck bridge typically has a number of array elements which are intended to be resident within the aneurysm after the device is deployed from the distal end of a catheter. Central to this invention is the use of array elements having differing flexibility or constituent members of the array elements, e.g., wires making up the array elements, which are of differing flexibilities. After deployment of this retainer, the aneurysm may be at least partially filled with vaso-occlusive devices such as helically wound coils.

BACKGROUND OF THE INVENTION

Different implantable medical devices have been developed for treating a number of ailments associated with body lumens. In particular, occlusive devices are useful in filling vascular or other body spaces. Some body spaces, such as vascular aneurysms, are formed due to a weakening in the wall of an artery. Often these aneurysms are the site of internal bleeding and, catastrophically, the site of strokes. A variety of different embolic agents are known as, at least arguably, suitable for treatment of these openings. These treatments are commonly known as "artificial vaso-occlusion".

One such class of embolic agents includes injectable fluids or suspensions, such as microfibrillar collagen, various polymeric beads, and polyvinylalcohol foam. These polymeric agents may additionally be crosslinked (sometimes in vivo) to extend the persistence of the agent at the vascular site. These agents are often introduced into the vasculature through a catheter. After such introduction, materials there form a solid space-filling mass. Although some provide for excellent short term occlusion, many are thought to allow vessel recanalization due to absorption of polymer into the blood. Another procedure in which a partially hydrolyzed polyvinylacetate (PVA) is dissolved in an ethanol solvent and injected into a desired vascular site is found in Park et al. (attorney docket no. 29025-20112.00) U.S. patent application Ser. No. 08/734,442, now U.S. Pat. No. 5,925,683 filed Oct. 17, 1996, for "LIQUID EMBOLIC AGENTS".

Other materials such as hog hair and suspensions of metal particles have also been suggested and used by those wishing to form occlusions.

Other materials including polymer resins, typically cyanoacrylates, are also employed as injectible vaso-occlusive materials. These resins are typically mixed with a radio-opaque contrast material or are made radio-opaque by the addition of a tantalum metal powder. Their use is fraught with problems in that placement of the mixture is quite difficult. These materials are ones which crosslink with the human body. Inadvertent embolisms in normal vasculature (due to the inability of controlling the destination of the resins) is not uncommon. The material is also difficult or impossible to retrieve once it has been placed in the vasculature.

Over the past few years, advancements in the artificial occlusions of vessels and aneurysms have occurred due to the delivery and implantation of metal coils as vaso-occlusive devices. Implantable metal coils that are useful as artificial occlusion devices in vasculature lumens or aneurysms are herein referred to as "vaso-occlusions coils".

Vaso-occlusive coils are generally constructed of a wire, usually made of a metal or metal alloy, that is wound into a helix. Many such devices are introduced in a stretched linear form to the selected target site through a catheter. The vaso-occlusive device assumes an irregular shape upon discharge of the device from the distal end of the catheter. A variety of vaso-occlusive coils and braids are known. For instance, U.S. Pat. No. 4,994,069, to Ritchart et al., shows a flexible, preferably coiled, wire for use in small vessel vaso-occlusion. Unlike vaso-occlusive coils used prior to that time, Ritchart taught a coil which is fairly soft and is delivered to the site using a pusher within a catheter lumen. Upon discharge from the delivery catheter, the coil may undertake any of the number of random or regular configurations used to fill the site. The coils are used for small vessel sites, e.g., 0.5–6 mm in diameter. The coils themselves are described as being between 0.010 and 0.030 inches in diameter. The length of the coil wire is typically 15 to 20 times the diameter of the vessel to be occluded. The wire used to make up the coils may be, for instance, 0.002 to 0.006 inches in diameter. Tungsten, platinum, and gold threads or wires are said to be preferred. These coils have a variety of benefits including the fact that they are relatively permanent, they may be easily imaged radiographically, they may be located at a well defined vessel site, and they can be retrieved.

It is common that these vaso-occlusive devices be delivered through microcatheters such as the type disclosed in U.S. Pat. No. 4,739,768, to Engelson. These microcatheters track a guidewire to a point just proximal or within the desired site for occlusion. The coil is advanced through the microcatheter (once the guidewire is removed) and out the distal end hole so to at least partially fill the selected space and create an occlusion.

In addition to vaso-occlusion devices or coils having predetermined secondary shapes that dictate in part their space filling mechanism, other vaso-occlusive coils have been disclosed that take on random shapes when expelled from a delivery sheath. One such type is a vaso-occlusive coil often referred to as "a liquid coil". One example of such a vaso-occlusive coil is disclosed in U.S. Pat. No. 5,690,666, to Berenstein et al. This patent describes a very soft and flexible coil which is flow-injectable through a delivery catheter using, e.g., saline solution.

In addition to the various types of space-filling mechanisms and geometries of vaso-occlusive coils, other particularized features of coil designs, such as mechanisms for delivering vaso-occlusive coils through delivery catheters and implanting them in a desired occlusion site, have also been described. The examples of categories of vaso-occlusive coils based upon their delivery mechanisms include pushable coils, mechanically detachable coils, and electrolytically detachable coils.

One example of the type of vaso-occlusive coil referred to above as the "pushable coil" is disclosed in Ritchart et al., discussed above. Pushable coils are commonly provided in a cartridge and are pushed or "plunged" from the cartridge into a delivery catheter lumen. A pusher advances the pushable coil through and out of the delivery catheter lumen and into the site for occlusion.

Mechanically detachable vaso-occlusive devices are typically integrated with a pusher rod or wire and are mechanically detached from the distal end of that pusher after exiting a delivery catheter. Examples of such mechanically detachable vaso-occlusive coils are found in U.S. Pat. No. 5,261,916, to Engelson, or U.S. Pat. No. 5,250,071, to Palermo.

Finally, examples of electrolytically detachable vaso-occlusive devices may be found in U.S. Pat. Nos. 5,122,136 and 5,354,295, each to Guglielmi et al. In these devices, the vaso-occlusive portion of the assembly is attached to a pusher via a small electrolytically severable joint. The electrolytically severable joint is severed by the placement of an appropriate voltage on the core wire. The joint erodes in preference either to the vaso-occlusive device itself or to the pusher core wire. The core wire is often simply insulated to prevent the electrolytic response caused by the imposition of electrical current.

Further improvement upon the electrolytical detachment mechanism described just is found in U.S. Pat. Nos. 5,643,254 and 5,669,905, to Scheldrup et al. These patents describe superimposing a modest alternating current upon the direct current signal. A sensing circuit monitors the alternating current as an indicator of the progression of coil detachment.

Improvements in enhancing the thrombogenic or other occlusive tissue response to metal coils has also been disclosed. For example, vaso-occlusive coils having fibers attached thereto are known—see, for example, U.S. Pat. No. 5,226,911, to Chee et al.

Each of the devices described above may be used in the treatment by occlusion of aneurysms. As noted above, aneurysms present particularly acute medical risk due to the dangers of potential rupture of the thin wall inherent in such an aneurysm. Occlusion of aneurysms by the use of vaso-occlusive coils without occluding the adjacent artery is a special challenge and is a desirable method of reducing such risk of rupture.

As noted above, the use of vaso-occlusive coils in treating aneurysms is widespread. These vaso-occlusive devices are placed in an aneurysm in the following fashion. A microcatheter is initially steered into or adjacent to the entrance of an aneurysm, typically aided by the use of a steerable guidewire. The wire is then withdrawn from the micro catheter lumen and replaced by the vaso-occlusive coil. The vaso-occlusive coil is advanced through and out of the microcatheter, desirably being completely delivered into the aneurysm. After, or perhaps during, delivery of such a coil into the aneurysm, there is a specific risk that a portion of the coil might migrate out of the aneurysm entrance zone and into the feeding vessel. The presence of such a coil in that feeding vessel may cause the undesirable response of causing an occlusion there. Also, there is a quantifiable risk that the blood flow in the vessel and aneurysm may induce movement of the coil farther out of the aneurysm, resulting in a more developed embolus in the patent vessel.

One type of aneurysm, commonly known as a "wide neck aneurysm" is known to present particular difficulty in the placement and retention of vaso-occlusive coils. Wide neck aneurysms are herein referred to as aneurysms of vessel walls having a neck or a "entrance zone" from the adjacent vessel, which entrance zone has a diameter that either: (1) is at least 80% of the largest diameter of the aneurysm; or (2) is clinically observed to be too wide effectively to retain vaso-occlusive coils that are deployed using the techniques discussed above.

Furthermore, vaso-occlusive coils lacking substantial secondary shape strength may be difficult to maintain in position within an aneurysm no matter how skillfully they are placed.

There are few disclosed devices for maintaining the presence of vaso-occlusive coils within an aneurysm. One such device is shown in U.S. Pat. No. 5,980,514, Kupiecki et al for "ANEURYSM CLOSURE DEVICE ASSEMBLY". Kupiecki et al describes a number of devices all which are said to be placed within the lumen of a feed vessel exterior to the aneurysm so to retain coils within the aneurysm cavity. That is to say that the retainer device is released in the vessel exterior to the aneurysm. The device is held in place via the presence of radial pressure on the vessel wall. After the device is released and set in an appropriate place, a microcatheter is inserted into the lumeri behind the retainer device and the distal end of the catheter is inserted into the aneurysm cavity. One or more vaso-occlusive devices is introduced into the aneurysm cavity. The retainer device maintains the presence of those vaso-occlusive devices within the aneurysm no matter whether the aneurysm is a large mouth aneurysm or not.

Another device for closing an aneurysm is found in U.S. Pat. No. 5,749,894, to Engelson et al, for "ANEURYSM CLOSURE METHOD". In this procedure, a vaso-occlusive device such as a coil or braid has on its outer surface a polymeric composition which may be reformed or solidified in situ within the human body. The device is simply inserted into the aneurysm and the polymer is then reformed, e.g., by the application of light, to melt or otherwise to reform the polymer exterior to the vaso-occlusive device. The vaso-occlusive device then sticks to itself at its various sites of contact and forms a rigid whole mass within the aneurysm.

There are a variety of other vaso-occlusive coils and devices which may be specified herein. The material provided above is only exemplary of the patents and publications dealing with such devices. No coil retainer device of the structure described herein is seen in any of the references described above.

SUMMARY OF THE INVENTION

This invention includes an implantable medical device both, or either, useful for retaining other occlusion devices at an occlusion site, such as an aneurysm, and at least partially closing the selected site by itself. The invention includes related methods of introducing and installing that medical device at the occlusion site. Combinations of the retainer device and its included vaso-occlusive material or device are also an aspect of the invention. In particular, the invention involves an implantable retainer which is deliverable through an elongated tubular delivery device such as a vascular catheter. The implantable retainer may include a core wire having both a proximal end and a distal end. At the distal end is a joint which allows the inventive neck bridge to be disengaged from the core wire. The joint itself extends between the distal end of that core wire and a number of array elements. The joint may be of a type which is electrolytically severable upon application of a suitable current to the joint. This type of joint is comparatively more electrolytically dissolvable or erodible in body fluids when a current is applied, than are any of the rest of the implantable retainer components. Finally the retainer assembly itself has a number of array elements which are of a shape (a first or delivery shape) which is deployable through a delivery catheter and, upon exit from the distal end of that catheter, readily assumes a secondary shape desirably conforming to the interior shape of the aneurysm catheter. Central to this invention is the use of array elements which vary in flexibility. The wires forming the array elements may differ in flexibility from array element to array element.

When using the preferred electrolytic joint, electrolysis of the severable joint permits placement of the retainer assembly at the aneurysm and removal of the attached delivery apparatus. Placement of the vaso-occlusive device to be retained in the aneurysm may then be had by simply introducing the vaso-occlusive device and its delivery tubular member between the array elements in the aneurysm.

The array elements themselves may be loops or may be arms which simply extend from the joint into the aneurysm cavity. It is within the scope of this invention that the retainer assembly include a number of "exterior" array members which, in general, extend radially from the region of the joint and are intended to remain in the feed vessel—not in the aneurysm—after deployment. These exterior loops define, with the interior array elements an annular area between them into which the rim or mouth of the aneurysm may fit.

The various portions of the device may be made to be radio-opaque by the choice of materials or by such other procedures as by wrapping the components in a radio-opaque wire or ribbon.

DESCRIPTION OF THE INVENTION

This invention involves a device and procedure for solving both the problems of closing aneurysm openings and of stabilizing the structure and placement of vaso-occlusive devices when they are placed in an aneurysm. These retaining devices generally are intended to prevent the migration of one or more occlusion devices such as coils from a target occlusion site, by forming a barrier at the entrance zone to the target site from a feeding vessel. The remainder of the retainer device which is remote from the mouth generally provides stability to the portion of the device which is in the mouth of the aneurysm.

Figure 1A:
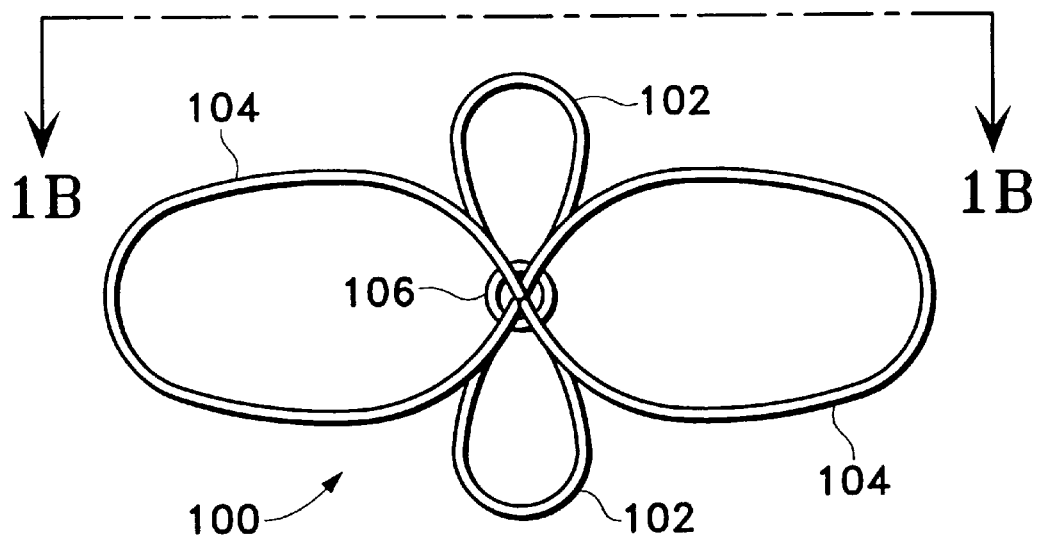
FIGS. 1A and 1B are respectively a top view and a side view of a variation of the inventive aneurysm retainers.
Figure 1B:
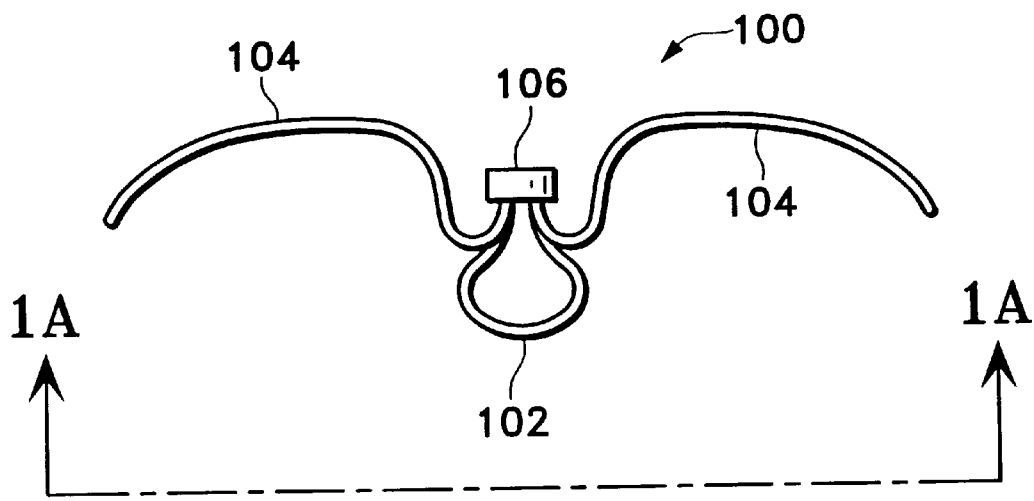

FIGS. 1A and 1B show a most typical but simple variation of the inventive device (100). The retainer assembly (100) has a shape which desirably approximates that of the mouth of the aneurysm into which it is placed. Specifically, the retainer device (100) has a plurality of array elements (102, 104) which extend from the preferred electrolytic joint (106) and form a loop which comes around to join itself back in the vicinity of electrolytic joint (106). It is, of course, permissible to use joints other than electrolytic joints in place of (106), e.g., joints which rely upon mechanical joining for structural certainty. However, joint (106) is desirably electrolytically severable because such joints are very functionally flexible in their deployment. That is to say, that should the aneurysm retainer somehow be malplaced, the fact that core wire (not shown) may be used to withdraw this device back into its delivery catheter or other suitable delivery tubular member, is a very big benefit.

FIG. 1B, a side view of the inventive retainer (100), shows another aspect of this invention which is sometimes significant in use. In this variation, the various array members (102, 104) are indented from the patent artery. This configuration has at least two benefits. First of all, the joint itself is not placed in the feed artery and should not cause the creation of an embolus in that vessel with the danger of subsequent blockage. Furthermore, the plurality of array wires (as may be shown from the top view in FIG. 1A) form what might be characterized as a skeletal funnel at the top of the retainer device (100) and consequently in the aneurysm itself, placement or re-placement of the feed catheter in the retainer device so to permit introduction of the vaso-occlusive member (not shown) into the interior volume of the aneurysm retainer device is simplified.

This variation of the invention as well as the others discussed below, are delivered through a tubular member such as a catheter. The shape of the device shown in FIG. 1A is the so-called secondary shape found after the retainer device (100) has been pushed from the distal end of the delivery device. The retainer device (100) generally has a relatively linear shape as is pushed through catheter. This primary or delivery shape is essentially the shape of the interior of the catheter during the delivery step. After deployment, the device assumes its secondary shape as is seen in FIG. 1A.

To undergo such massive changes in shape, it is usually preferable that the interior array elements (102) be produced of material such as a superelastic alloy. Superelastic or pseudoelastic shape recovery alloys are well known in this art. For instance, U.S. Pat. Nos. 3,174,851; 3,351,463; and 3,753,700 each describe one of the more well known superelastic alloys, also known generically as nitinol. These alloys are characterized by their ability to be transformed from an austenitic crystal structure to a stress-induced-martensitic (SIM) structure at certain temperatures and then return elastically to the austenitic shape when the stress is removed. These alternating crystal structures provide the alloy with its superelastic properties. The alloy mentioned in the three patents just above, is a nickel-titanium alloy. It is readily commercially available and undergoes the austenitic-SIM-austenitic transformation in a variety of temperatures between −20° C. and +30° C.

These alloys are especially suitable because of their capacity to recover elastically—almost completely—to the initial configuration once the stress is removed. Typically, in these services, there is little plastic deformation even at relatively high strains. This allows the retainer device (100) to undertake substantial bends both as it is collapsed to enter the tubular delivery device and as it undertakes further bending in passing through turns in the vasculature. In spite of this bending, it returns to its original shape once the bend has been traversed without retaining a kink or a bend.

Of the superelastic alloys currently available, we consider a preferred material to be nominally 50.6±2% nickel and most of the remainder, titanium. Up to about 5% of the alloy may be another member of the iron group of metals, particularly chromium and iron. The alloy shouldn't contain more than about 500 parts per million of oxygen, carbon, or nitrogen. The transition temperature of this material is not particularly important, but it should be reasonably below the typical temperature of the human body so to allow it to be in its austinitic phase during use. The diameter of the wires or ribbons making up the array elements preferably are smaller than about 0.010 inches in diameter. As will be discussed below, the typical superelastic alloy is not always completely visible under fluoroscopy. Consequently, it is often desirable to add some type of a covering to improve the radio-opacity of the device. Radio-opaque metals such as gold and platinum are well known.

Although we have discussed the concept that these devices are desirably made from superelastic alloys, other metals may in certain circumstances be appropriate. Such metals include a number of the stainless steels and other highly elastic, if not superelastic alloys. Furthermore, it is within the scope of this invention that the array elements (102, 104) be of polymeric material. Polymeric materials are somewhat easier to work with in forming the device and may also suitable for maintaining the vaso-occlusive devices at an appropriate site within the aneurysm. Such materials as polyethylene, polypropylene, polytetrafluoroethylene, various of the Nylons, and the like would be easily chosen by one having ordinary skill in this art for the purposes shown herein.

Central to the invention is the use of array elements, or their constituent wires or ribbons, which differ in flexibility. That is to say that in the variation shown in FIGS. 1A and 1B, the axial array elements (104) may less stiff (more flexible) than the circumferential array elements (102). This variation provides for a stabilization of the inventive neck bridge (100) due to the relatively firmer pressure placed on the neck by the circumferential array elements (102) and the softer, but more widely spread, pressure from the axial array elements (104).

Although it is quite desirable from the perspective of the physician user to have a device which is symmetrical in providing pressure distally and proximally on the aneurysm and side to side as well, such is not absolutely necessary. Opposing pairs of array members having the same flexibility or composed of constituent wires or ribbons having the same flexibility are highly desired but not always necessary depending upon the situation.

Although the array elements (102, 104) are generally shown to be regular and of the approximate same shape on each of the axes through the retainer device (100), such obviously need not be the case. It is within the scope of this invention that the retainer assembly be irregular in shape so to fit the shape of an irregular aneurysm. Placement of such devices must be done with some care, but it is within the purview of one having ordinary skill in the art with some instruction.

Figure 2:
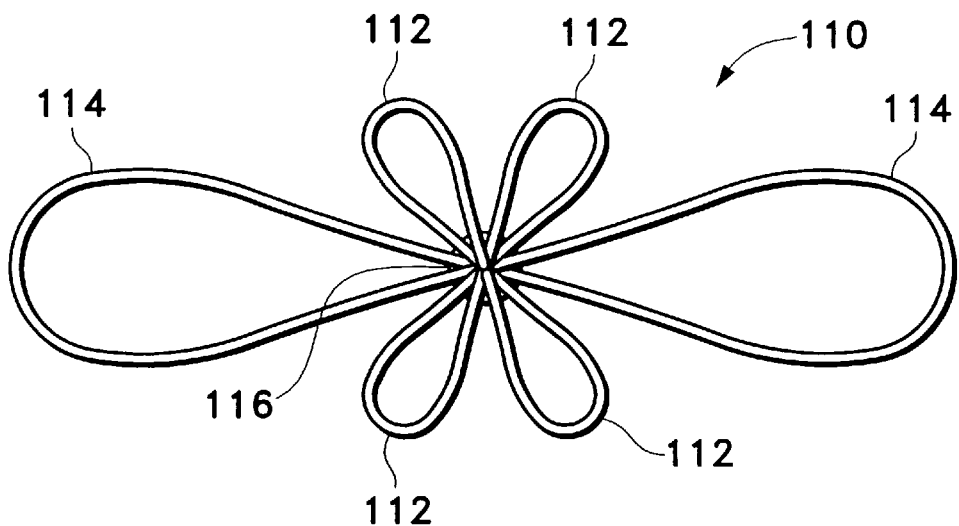
FIG. 2 is a top view of a variation of the inventive aneurysm retainer.

FIG. 2 shows another variation of the inventive retainer assembly (110) in which the circumferential array elements (110) are multiple. Axial array element (112) is of the same general shape as those shown in FIG. 1A and FIG. 1B. These circumferentially extending loops (112) are intended to fit within the aneurysm and provide lateral stability to the placement of the retainer device (110). A pair of axial array elements (114) is shown in FIG. 2. The invention is, obviously, not so limited.

The generally circumferential array elements (112) may have larger loops than those shown in the Figure. Again, this device is desirably situated in its secondary form so that the remainder of any attachment element, attached formerly joint (116) after separation from the feed or core wire, will not extend into the feeder vessel for this aneurysm. This retainer assembly (110) may be used to help close an aneurysm which is of substantial length but nominal width.

Again, it is desirable that the circumferential array elements (112) be of a different flexibility than the axial array elements (114) or be constructed of wires or ribbons having differing flexibilities.

Figure 3:
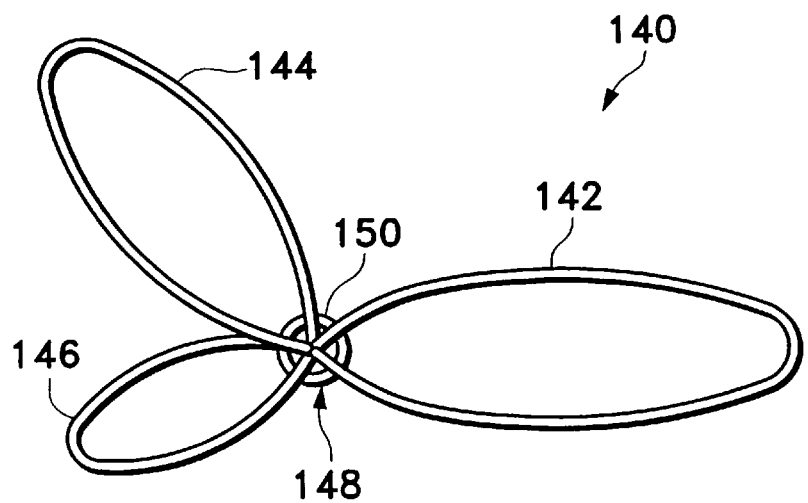
FIG. 3 is a top view of the inventive aneurysm retainer.

FIG. 3 shows still another variation of the inventive device (140). This variation shows multiple array members of varying size (142, 144, 146) attached to a generally central detachment joint (148), which joint may be of a design such as those discussed above.

Although the overall configuration of this device (140) as shown in FIG. 3 may be indented at the top in the same manner as the variations shown in FIG. 1B, this neck configuration is shown for purposes of completing the variations of this invention. The array members (142, 144, 146) to a core wire (as shown below) via a ferrule (150) perhaps by crimping or perhaps by welding the devices components together.

Figure 4:
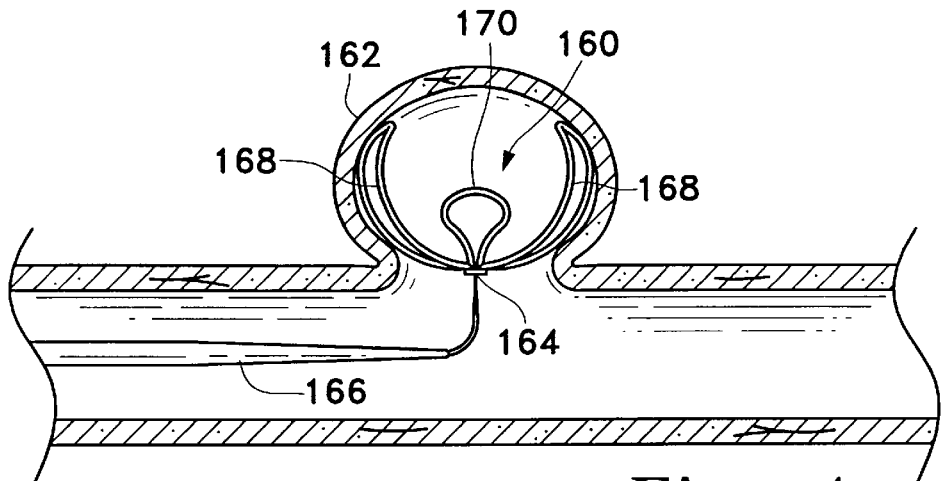
FIG. 4 is a partial side view of the inventive aneurysm retainer placed in an aneurysm.

FIG. 4 shows the placement of an inventive device (160) in a wide-mouthed aneurysm (162). This neck bridge (160) lacks the detent at the joint shown in the variations above. However, the core or delivery wire (166) attached to the detachable joint (164) is shown. It should be noted that the axial array members (168) lay along the aneurysm wall and the circumferential members (170) are generally across the mouth of the aneurysm. In most instances, the back wall of the aneurysm is especially weak and the neck of the aneurysm is considered to be the strongest retention point.

Figure 5A:
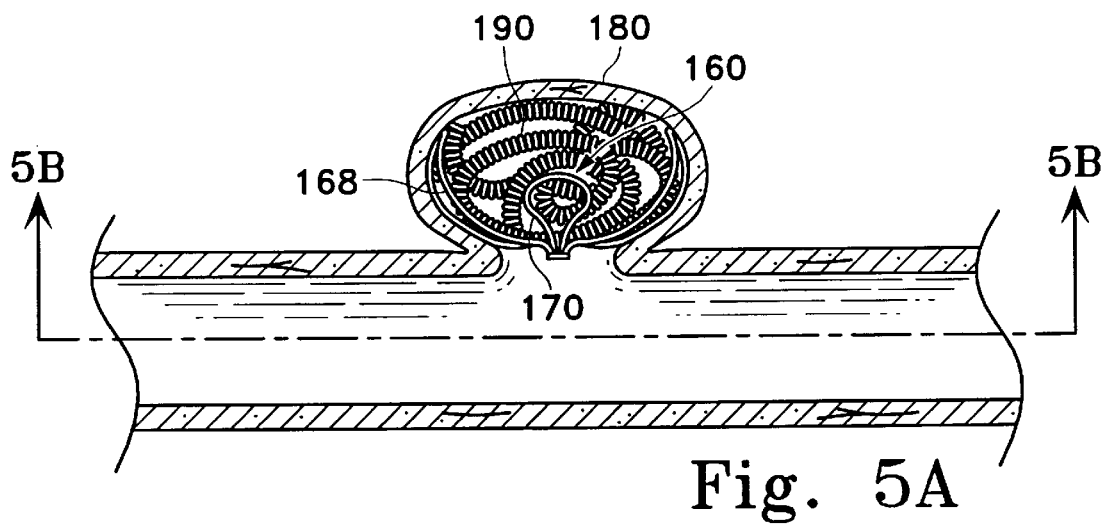
FIGS. 5A and 5B show respectively a partial cross sectional side view and top view of a variation of the inventive aneurysm retainer within an aneurysm.
Figure 5B:
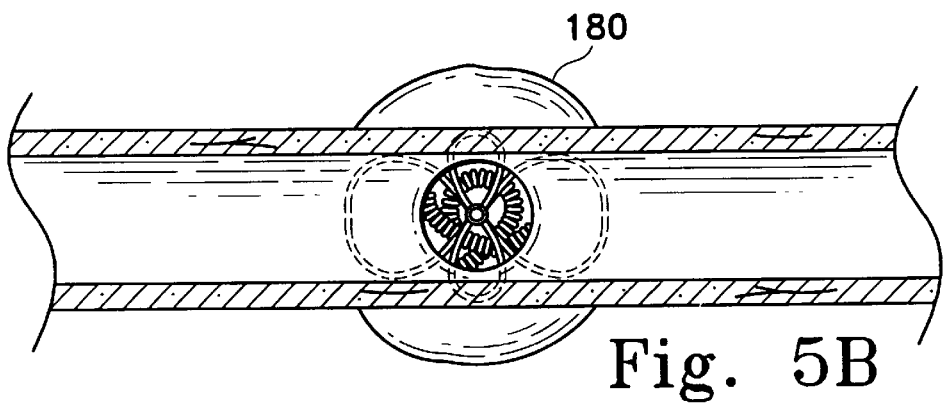

FIGS. 5A and 5B show the placement of the variation (160) of the inventive device in a narrow neck aneurysm. FIG. 5A is a cross-section and FIG. 5B is a top-view cross section centering on the aneurysm mouth as viewed from mid-artery. Again, this shows the axial or longitudinal array members (168) extending in a direction along the axis of the artery and the circumferential array members (170) extending around a portion of the circumference of the aneurysm generally, in this case, orthogonal to the axis of the artery axis. Finally, the aneurysm is shown having a vaso-occlusive device, in this instance a helical coil, in the volume of the aneurysm (180).

Figure 6A:
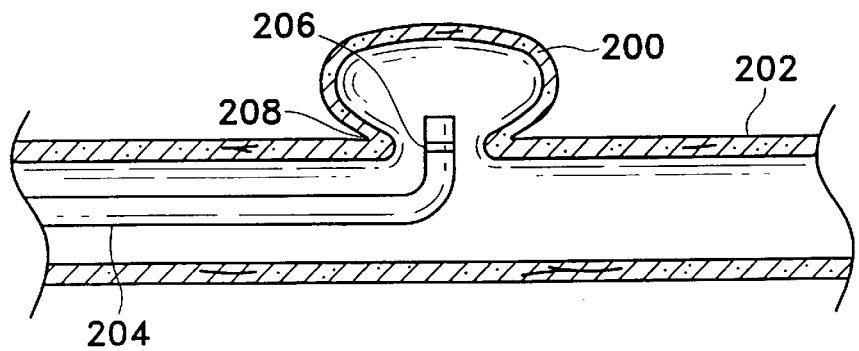
FIGS. 6A to 6E show a method of deploying a device made according to this invention and the vaso-occlusive devices therein.
Figure 6B:
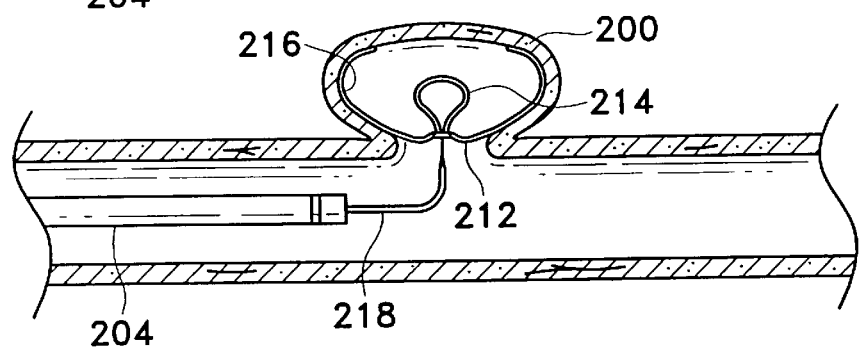

This device may be deployed in the following manner. FIG. 6A shows a berry aneurysm (200) emanating from the wall of an artery (202). A catheter (204) is shown having radio-opaque band (206) at its distal end. The distal end of catheter (204) extends into the mouth (208) of the aneurysm (200). FIG. 6B shows a retainer device (212) having a shape similar to those discussed above. This variation of the inventive retainer (212) has circumferential array members (214) and axial array members (216). It should probably be apparent that the various array members should not pinch the aneurysm in any very meaningful or deleterious way, lest some type of rupture occur.

Figure 6C:
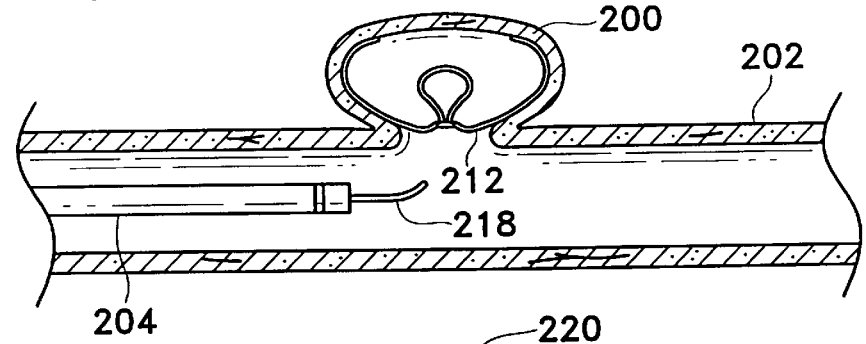

In FIG. 6C, it can be seen that the voltage has been applied to core wire (218), and the electrolytic joint has been dissolved. The core wire (218) is then withdrawn from catheter (204) and discarded. It may be also seen in FIG. 6C that the region of the joint adjacent the retainer device (212) is recessed out of the flow of artery (202).

The electrolytic severable joint may also be called a sacrificial link. Core wire (210) is typically coated with an electrical insulator which is not susceptible to dissolution via electrolysis in blood or other ionic media. Suitable coatings for core wire (210) include such insulating materials as the polyfluorocarbons (e.g., Teflon), polyurethane, polyethylene, polypropylene, polyimides or other suitable polymeric materials. The sacrificial joint is not coated with such an insulator and is of a material which is susceptible to electrolytic dissolution in blood. The sacificial joint may be a simple un-insulated continuation of, e.g., stainless steel core wire (210), which has been insulated proximally of the joint. It should also be apparent that the sacrificial joint is more susceptible to electrolysis than are the array elements. Further discussion of construction of, placement of, and other physical details of such a joint may be found in U.S. Pat. No. 5,122,136 to Guglielmi et al.; U.S. Pat. No. 5,354,295 to Guglielmi et al.; U.S. Pat. No. 5,624,449, to Pham et al., and others.

Figure 6D:
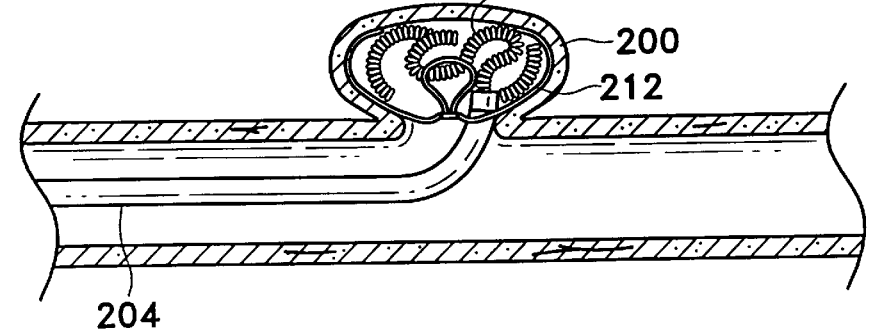

In FIG. 6D, catheter (204) has been re-introduced into the neck of aneurysm (200) and a number of vaso-occlusive devices—in this case, coils (220)—have been introduced into the volume formed by retainer assembly (212).

Figure 6E:
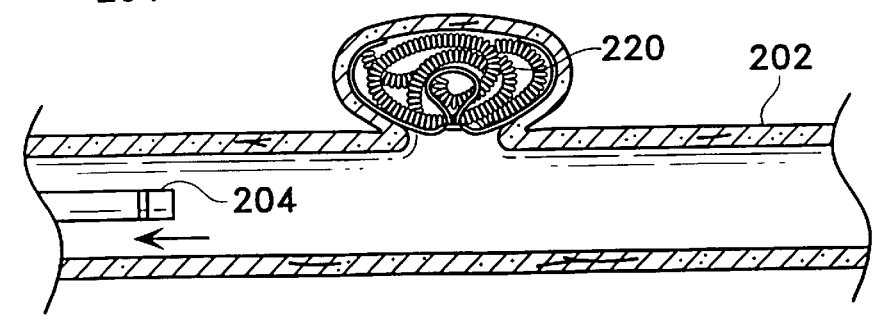

FIG. 6E show the withdrawal of catheter (204) from the feed vessel with the implantation of vaso-occlusive coils (220) and their stabilizing retainer (212) complete.

Many alterations and modifications may be made by those of ordinary skill in this art, without departing from the spirit and scope of this invention. The illustrated embodiments have been shown on for purposes of clarity and the example should not be taken as limiting the invention as defined in the following claims, which are intended to include all equivalents, whether now or later devised.

We claim:

1. An implantable retainer bridge, deliverable via an elongate tubular delivery device, of a size and overall flexibility to safely lodge at the mouth of a vascular aneurysm, and suitable for retaining at least a vaso-occlusive device in a vascular aneurysm, comprising:

a) a detachable joint located centrally to a plurality of array elements, and detachable from a core wire delivery element, and b) said plurality of array elements extending outwardly from and fixedly attached to said detachable joint, each of said array element comprising a wire extending away from said detachable joint and forming a loop extending from and returning back to said detachable joint.

2. The implantable retainer bridge of claim 1, wherein said detachable joint comprises an electrolytically severable joint suitable for separating said core wire delivery element from said implantable retainer upon application of a suitable current to said joint, said joint being comparatively more susceptible to electrolytic severability than said core wire delivery element and said plurality of array elements.

3. The implantable retainer bridge of claim 1, wherein said detachable joint comprises a mechanically detachable joint suitable for separating said core wire delivery element from said implantable retainer.

4. The implantable retainer bridge of claim 1, wherein said implantable retainer has a first delivery shape when retained within said elongate tubular delivery device and having a distal delivery end and a proximal delivery end, and a second deployed shape, different than first delivery shape, when said implantable retainer is not retained within said tubular delivery device and having a distal deployed and an proximal deployed end, said plurality of array elements extends outwardly from said joint in said second deployed shape.

5. The implantable retainer bridge of claim 2 further comprising a core wire delivery element, wherein said core wire delivery element is covered with an electrical insulation layer from near its proximal end to near its distal end.

6. The implantable retainer bridge of claim 1, wherein said plurality of array elements comprise platinum.

7. The implantable retainer bridge of claim 1 wherein said plurality of array elements comprise tantalum.

8. The implantable retainer bridge of claim 1 wherein said plurality of array elements comprise stainless steel.

9. The implantable retainer bridge of claim 1 wherein said plurality of array elements comprise a super-elastic alloy.

10. The implantable retainer bridge of claim 1 wherein at least a portion of said plurality of array elements is covered by radio-opaque material.

11. The implantable retainer bridge of claim 7 wherein said radio-opaque material is platinum.

12. The implantable retainer bridge of claim 1, where said plurality of array elements comprises at least one multiple array pair.

13. The implantable retainer bridge of claim 1, where said plurality of array elements comprises at least one array pair.

14. The implantable retainer bridge of claim 1, where said plurality of array elements comprises at least two elements of differing flexibility.

15. The implantable retainer bridge of claim 1, where said plurality of array elements comprises at least two elements each having said loops of differing sizes.

16. The implantable retainer bridge of claim 1, where said detachable joint is indented from said plurality of array elements.

* * * * *